(12) United States Patent
Ollivier et al.

(10) Patent No.: US 6,852,883 B2
(45) Date of Patent: Feb. 8, 2005

(54) METHOD FOR MAKING ALKANESULPHONYL CHLORIDES

(75) Inventors: Jean Ollivier, Arudy (FR); Gisele Haurat, Arthez de Bearn (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/380,326

(22) PCT Filed: Sep. 10, 2001

(86) PCT No.: PCT/FR01/02799

§ 371 (c)(1),
(2), (4) Date: Jul. 25, 2003

(87) PCT Pub. No.: WO02/22564

PCT Pub. Date: Mar. 21, 2002

(65) Prior Publication Data

US 2004/0015019 A1 Jan. 22, 2004

(30) Foreign Application Priority Data

Sep. 13, 2000 (FR) ............................................ 00 11648

(51) Int. Cl.$^7$ ............................................ C07C 309/04
(52) U.S. Cl. ........................ 562/829; 562/821; 562/827; 562/828
(58) Field of Search ................................ 562/829, 828, 562/827, 821

(56) References Cited

U.S. PATENT DOCUMENTS

| | | |
|---|---|---|
| 3,248,423 A | 4/1966 | Stratton et al. |
| 3,600,136 A | 8/1971 | Giolito et al. |
| 3,626,004 A | 12/1971 | Guertin |
| 3,993,692 A | 11/1976 | Giolito et al. |
| 4,280,966 A | 7/1981 | Hubenett |
| 4,956,494 A * | 9/1990 | Husain et al. ............... 562/118 |
| 6,441,229 B1 * | 8/2002 | Shaw ........................ 562/829 |

FOREIGN PATENT DOCUMENTS

| | | |
|---|---|---|
| DE | 1 811 768 | 9/1969 |
| DE | 2 845 918 | 5/1980 |
| FR | 1 598 279 | 8/1970 |
| FR | 2 083 422 | 3/1971 |
| JP | 52-8283 | 1/1977 |
| JP | 52-008283 | 1/1977 |
| JP | 52-20970 | 2/1977 |
| JP | 52-020970 | 2/1977 |

OTHER PUBLICATIONS

CA:135:212601 abs of JP2001247537 Sep. 11, 2001.*
CA:140:6407 abs of JP2003342252 Dec. 2003.*
Bradley D. Christie, et al., "Synthesis of Optically Pure Pipecolates from L–Asparagine. Application to the Total Synthesis of (+)– Apovincamine through Amino Acid Decarbonylation and Iminium Ion Cyclization", J. Org. Chem. 1985, 50, pp. 1239–1246.
International Preliminary Examination Report (PCT/IPEA/ 409 and PCT/IPEA/416) (translated) issued for PCT/FR01/ 02799, 2002.

* cited by examiner

Primary Examiner—Shailendra Kumar
(74) Attorney, Agent, or Firm—Smith, Gambrell & Russell, LLP

(57) ABSTRACT

In the process according to the invention for the manufacture of an alkanesulphonyl chloride $RCH_2-SO_2Cl$ by oxidative chlorolysis of the corresponding mercaptan $RCH_2-SH$, the mercaptan and water are introduced into the reaction mixture in the form of a dispersion of water in the mercaptan.

This makes it possible to obtain both an alkanesulphonyl chloride of very good quality and a hydrochloric acid of commercial grade.

8 Claims, No Drawings

METHOD FOR MAKING ALKANESULPHONYL CHLORIDES

This application is an application under 35 U.S.C. §371 of PCT/FR01/02799, filed Sep. 10, 2001, now WO02/22564.

FIELD OF THE INVENTION

The present invention relates to the field of alkanesulphonyl chlorides and has more particularly as subject-matter their synthesis by oxidative chlorolysis or the corresponding mercaptan in the presence of water according to the overall reaction:

$$RCH_2\text{—}SH + 2H_2O + 3Cl_2 \rightarrow RCH_2\text{—}SO_2Cl + 5HCl$$

BACKGROUND OF THE INVENTION

Consultation of the prior art shows that this synthesis of alkanesulphonyl chlorides from mercaptans is carried out, under batchwise or continuous conditions, by bringing chlorine and the mercaptan into contact in a concentrated aqueous hydrochloric acid solution (Patents FR 1 598 279, DE 1 811 768, U.S. Pat. No. 3,626,004, JP 52-020970, U.S. Pat. Nos. 3,600,136 and U.S. Pat. No. 3,993,692) or in pure water (Patents DE 2 845 918, JP 52-008283, U.S. Pat. No. 3,248,423 and U.S. Pat. No. 4,280,966), the objective being to obtain an alkanesulphonyl chloride with a good yield and the best possible purity, that is to say while avoiding the formation of troublesome by-product or intermediate compounds. One of the most troublesome among these compounds is 1-chloroalkanesulphonyl chloride RCHCl—SO$_2$Cl; alkanesulphinic acid RCH$_2$—SO$_2$H, alkyl alkanethiosulphonate RCH$_2$—SO$_2$—SCH$_2$R and alkanesulphinyl chloride RCH$_2$—SOCl, optionally in combination with their α-chlorinated derivatives, are also encountered. These compounds, for the most part of low stability, are the source of the colouring of alkylsulphonyl chloride over time.

In order to avoid the formation of such compounds, it is advantageous to operate with an excess of water. This makes it possible to greatly restrict the formation of 1-chloroalkanesulphonyl chloride and alkanesulphinic acid, alkyl alkanethiosulphonate or alkanesulphinyl chloride is no longer encountered in alkanesulphonyl chloride prepared in this way.

The hydrochloric acid produced by the reaction remains predominantly trapped in the water, which has to be introduced in large amounts in order to ensure good selectivity for alkanesulphonyl chloride. This is one of the reasons why the abovementioned Patents FR 1 598 279, DE 1 811 768, U.S. Pat. No. 3,626,004, JP 52-020970, U.S. Pat. No. 3,600,136 and U.S. Pat. No. 3,993,692 recommend introducing the water in the form of a concentrated aqueous hydrochloric acid solution, so as to recover a pure hydrochloric acid gas, the impurities being predominantly trapped in the acidic aqueous phase.

However, as explained above, the formation of the α-chlorinated derivative RCHCl—SO$_2$Cl, a troublesome impurity for the applications of the chloride RCH$_2$—SO$_2$Cl which is very difficult to separate by standard purification techniques, is thus promoted.

On analysing the prior art, it emerges that the processes provided do not take into account the quality of the hydrochloric acid coproduced and that there was no interest in its enhancement in value. Recovered after separation by settling of the reaction mixture, it accumulated various by-products, such as sulphuric acid, sulphinic and sulphonic acid, a small amount of alkanesulphonyl chloride, and the like, and it is therefore unsuitable in this state for marketing.

In summary:
1) when the water is introduced in the form of a concentrated aqueous hydrochloric acid solution, a gaseous HCl of good quality is recovered but the alkanesulphonyl chloride obtained comprises relatively large amounts of the α-chlorinated derivative RCHCl—SO$_2$Cl;
2) when the water is introduced pure, the alkanesulphonyl chloride is of very good quality (very little 1-chloroalkanesulphonyl chloride) but the aqueous phase recovered is contaminated by sulphuric acid and organic compounds and the concentration of the hydrochloric acid obtained does not necessarily correspond to a commercial specification.

DESCRIPTION OF THE INVENTION

An aim of the present invention is thus to combine the respective advantages of the processes with pure water and of the processes using a concentrated aqueous hydrochloric acid solution, so as to obtain both an alkanesulphonyl chloride of very good quality and a hydrochloric acid of commercial grade.

It has now been found that this aim can be achieved by dispersing water beforehand in the mercaptan and by injecting the dispersion thus obtained into the reaction mixture.

A subject-matter of the present invention is thus a process for the manufacture of an alkanesulphonyl chloride RCH$_2$—SO$_2$Cl by oxidative chlorolysis of the corresponding mercaptan RCH$_2$—SH, characterized in that the mercaptan and water are introduced into the reaction mixture in the form of a dispersion of water in the mercaptan.

This dispersion can be obtained, for example, by mechanical stirring, by a static mixer or by any other means known to a person skilled in the art for obtaining a fine dispersion of water in the organic mercaptan phase. The dispersion can optionally be stabilized by the addition of a small amount (500 to 1 000 ppm with respect to the weight of makeup water) of a surfactant, such as, for example, octanesulphonic acid, decanesulphonic acid, dodecanesulphonic acid or the sodium salt of such an acid.

Although the water:mercaptan molar ratio can range from 0.5:1 to 5:1, the amount of water dispersed in the mercaptan is advantageously that which corresponds to the stoichiometry of the reaction mentioned above, i.e. two moles of water per mole of mercaptan. With a water:mercaptan molar ratio equal to 2:1, the content by mass of water in the dispersion will vary, for example, from 28.5% for butyl mercaptan to 17.1% for decyl mercaptan (23.3% for hexyl mercaptan, 19.7% for octyl mercaptan, and the like).

In accordance with the process according to the invention, the dispersion of water in the mercaptan is subsequently injected into the reaction mixture, which has been rendered as homogeneous as possible and which is composed initially of a concentrated solution of hydrochloric acid in water (33 to 40%). The concentration of alkanesulphonyl chloride in the reaction mixture can range from 0 to 50%; it varies according to the degree of progress of the reaction and the operating method.

The process according to the invention can be implemented under batchwise conditions or under continuous conditions. Under batchwise conditions, a hydrochloric acid (36 to 40%) heel is placed beforehand in the reactor and then, with vigorous stirring, the water/mercaptan dispersion and the chlorine are gradually introduced with a chlorine- :mercaptan molar ratio preferably equal to 3:1. The gaseous hydrochloric acid produced during the reaction is scrubbed out with water in a column of the type well known to a person skilled in the art and the alkanesulphonyl chloride produced is recovered after settling and separation of the acidic aqueous phase, which can optionally be recycled for another operation.

The implementation of the process according to the invention under continuous conditions requires two reactors in series, the reaction being essentially carried out in the first (main reactor) and the second (finishing reactor) being used to remove the nonoxidized intermediates. A turnround of hydrochloric acid (33 to 40% in water) is created, which turnround will condition the residence time in the reactor and the finisher. The reactants are introduced into the main reactor in the same way as under batchwise conditions. Downstream of the main reactor, a gas-liquid separator makes it possible to recover the gaseous hydrochloric acid, subsequently scrubbed out with water in a column provided for this purpose. The finishing reactor, itself also stirred, receives an additional chlorine contribution and its contents subsequently pass into a separator for separating the sulphochloride from the concentrated aqueous hydrochloric acid solution, which is recycled using a pump.

The process according to the invention can be applied to the synthesis of alkanesulphonyl chlorides $RCH_2$—$SO_2Cl$ comprising from 2 to 12 carbon atoms, preferably 4 to 10. The $RCH_2$ radical is preferably a linear alkyl radical but it can also be branched, such as, for example, in the case of isobutyl mercaptan.

The following examples, in which the percentages shown are percentages by mass, illustrate the invention without limiting it.

EXAMPLE

The tests were carried out in a device comprising a reactor with a capacity of 10 litres equipped with a jacket connected to a cooling system, with a condenser, with a temperature recorder and with a mechanical stirrer comprising two rotors which can rotate at from 250 to 1 000 revolutions per minute. Gas (chlorine or nitrogen) is fed in by means of a pipe via a sintered glass sparger. The flow rate for the gas is controlled by a mass flowmeter under electronic control. Two metering pumps respectively inject the mercaptan and the makeup water into a static mixer, placed directly in the reaction medium such that the mercaptan/water emulsion does not have the time to separate.

The gas exiting from the condenser is introduced into a column for scrubbing out with water the hydrochloric acid produced by the reaction. A rotameter measures the total gas flow rate at the outlet of the reactor and the chlorine content of the gaseous effluent exiting from the reactor is measured using a UV spectrophotometer connected in line.

EXAMPLE 1

Preparation of n-octanesulphonyl Chloride Under Batchwise Conditions 5 200 grams (4.41 litres) of a 36% aqueous hydrochloric acid solution were place beforehand in the reactor and, after having brought this solution to 6° C. with vigorous stirring, the introduction of the water/n-octyl mercaptan dispersion (molar ratio 2/1) was begun and, at the same time, that of chlorine was begun, so that the chlorine/mercaptan molar ratio is equal to 3/1.

To convert 3 000 grams of an n-octyl mercaptan into n-octanesulphonic chloride, 4 362 grams of chlorine (61.5 mol) and 738 grams of water (41 mol) were introduced. The temperature, gradually raised to 20° C., was maintained at this level by virtue of the cooled jacket.

After having introduced, over 5 hours, all the desired amount of n-octyl mercaptan (3 000 g), the feeding of the mercaptan and that of the makeup water were halted but the injection of the chlorine was continued for one hour at only 5% of its initial flow rate, while continuing to stir, in order to bring the oxidation of the synthetic intermediates to octane-sulphonyl chloride to completion.

9 974 g of a two-phase mixture, composed of 4 362 g of crude n-octanesulphonyl chloride, 66 g of HCl dissolved in this chloride and 5 546 g of a 40% hydrochloric acid solution, were recovered in the reactor. Settling for one hour made it possible to separate the two organic and aqueous phases.

After stripping the HCl and the traces of chlorine which it comprises, analysis of the organic phase yielded the following results:

| | |
|---|---|
| octanesulphonyl chloride: (production: 4 231 g) | 97% |
| 1-chlorooctanesulphonyl chloride: | 0.25% |
| 1-chlorooctanesulphinyl chloride: | 0.1% |
| octyl octanethiosulphonate: | 0.1% |
| water: | 0.1% |
| octanesulphonic acid: | 0.2% |
| octanesulphinic acid: | 0.1% |
| isooctanesulphonyl chloride: | 0.3% |

(originates from the isomercaptan present in the starting reactant)

other heavy products: 1.85%

For a total production of 3 739 g of hydrochloric acid, the balance sheet worked out as follows:

65.44 g dissolved in the crude octane-sulphonyl chloride 346.7 g trapped in the acidic aqueous phase, which they bring to an assay of 40%

3 327 g (i.e. 89% of the acid produced) scrubbed out with water to form 33% acid (9 981 g).

The acidic aqueous phase (5 546 g) had the following composition:

| | |
|---|---|
| HCl assay: | 40% |
| octanesulphonyl chloride: | 0.20% |
| sulphuric acid: | 0.26% |
| octanesulphonic acid: | 0.074% |
| octanesulphinic acid: | 0.023% | and can be recycled for another operation, with an addition of water, if necessary.

The scrubbed hydrochloric acid assayed 33% and did not comprise detectable traces of organic compounds. Because of its very low content of sulphuric acid (37 ppm), it was suitable for marketing.

Comparative Example 2

The preparation was carried out as in Example 1 but without the addition of water and while directly introducing the n-octyl mercaptan into the reaction mixture. To obtain complete conversion of the mercaptan and the reaction intermediates to octanesulphonyl chloride, the overall reaction time changed from six hours to nine hours and thus increased by 50%.

The purity of the octanesulphonyl chloride obtained under these conditions was only 92% (production: 4 013 g) and it comprised 4.65% of 1-chlorooctanesulphonyl chloride, 1.3% of octanesulphinyl chloride and of its chlorinated derivative, 1.2% of octanesulphinic acid and 0.5% of octyl octanethiosulphonate.

The purity of the 33% hydrochloric acid recovered in the scrubbing column is equivalent to that in Example 1.

Comparative Example 3

The preparation was carried out as in Example 1 but replacing the heel of 36% hydrochloric acid solution with a heel of pure water of the same mass (5 200 g) and introducing the n-octyl mercaptan alone (without water) into the reactor. The total reaction time was the same as that in Example 1.

The organic phase recovered assayed 97.5% of octanesulphonyl chloride (i.e. 4 230 g of octanesulphonyl chloride) and comprised only 0.2% of 1-chlorooctanesulphonyl chloride; the synthetic intermediates (octanesulphinyl chloride, octanesulphinic acid, octyl octanethiosulphonate) totalled only 1%.

7 435 g of acidic aqueous phase assaying 40% of hydrochloric acid were recovered, this aqueous phase being contaminated by 2 620 ppm of sulphuric acid, 740 ppm of octanesulphonic acid, 350 ppm of octane-sulphonyl chloride and a not insignificant amount of octanesulphinic acid which could not be quantitatively determined.

The pure hydrochloric acid fraction which reached the scrubbing with water only corresponded to 18.7% of the total acid produced, i.e. 700 g, giving 2 100 g of 33% solution with a purity equivalent of that of the acid obtained in Example 1.

The aqueous hydrochloric acid phase had a composition similar to that of the residual aqueous phase in Example 1. It is therefore not possible to have available 81.3% of the hydrochloric acid from the reaction without purifying the latter and thus increasing its cost price.

The main results obtained in the preceding examples are summarized in the following table, in which OSC denotes n-octanesulphonyl chloride and ClOSC denotes 1-chlorooctanesulphonyl chloride, for a production of 4 362 g of crude OSC.

| Example | Purity of the OSC (% by mass) | ClOSC content (% by mass) | Production of pure 33% hydrochloric acid |
|---|---|---|---|
| 1 | 97 | 0.25 | 9 981 g |
| 2 | 92 | 4.65 | 11 460 g |
| 3 | 97.5 | 0.20 | 2 100 g |

EXAMPLES 4, 5 and 6

Preparation of butane-sulphonyl chloride (BSC), hexanesulphonyl chloride (HSC) and decanesulphonyl chloride (DSC)

The preparations were carried out as in Example 1 with premixing of the mercaptan and the water before injecting them into the reaction mixture but replacing the n-octyl mercaptan with the same amount (3 000 grams) of n-butyl mercaptan, of n-hexyl mercaptan or of n-decyl mercaptan respectively. In all cases, the water heel was 5 200 grams.

The results obtained are collated in the following table, which shows the production of crude alkanesulphonyl chloride, its purity and its content of α-chlorinated derivative, and the production of 33% hydrochloric acid of commercial grade.

| Example | Alkanesulphonyl chloride | | | Content of α-chlorinated derivative (%) | Production of pure 33% hydrochloric acid |
|---|---|---|---|---|---|
| | Nature | Production | Purity (%) | | |
| 4 | BSC | 5 207 g | 98 | 0.12 | 16 900 g |
| 5 | HSC | 4 685 g | 97.3 | 0.16 | 12 622 g |
| 6 | DSC | 4 143 g | 97 | 0.30 | 8 189 g |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. Process for the manufacture of an alkanesulphonyl chloride $RCH_2$—$SO_2Cl$ by oxidative chlorolysis of the corresponding mercaptan $RCH_2$—SH, comprising introducing the mercaptan and water into a reaction mixture in the form of a dispersion of water in the mercaptan, wherein the reaction mixture is initially comprised of a concentrated aqueous hydrochloric acid solution, further wherein R is an alkyl group having from 2 to 12 carbon atoms.

2. Process according to claim 1, wherein the amount of water dispersed in the mercaptan is such that the water:mercaptan molar ratio is between 0.5:1 and 5:1.

3. Process according to claim 1, wherein chlorine is introduced in a chlorine:mercaptan molar ratio equal to 3:1.

4. Process according to claim 1, wherein R is a linear alkyl radical.

5. Process according to claim 2, wherein the ratio is equal to 2:1.

6. Process according to claim 1, wherein the solution has an HCl content of 33 to 40% by weight.

7. Process according to claim 1, wherein R comprises from 4 to 10 carbon atoms.

8. Process according to claim 1, wherein the alkanesulphonyl chloride is n-octanesulphonyl chloride.

* * * * *